(12) United States Patent
Greiving

(10) Patent No.: US 7,951,943 B2
(45) Date of Patent: May 31, 2011

(54) METHOD FOR PREPARING AND PURIFYING 3-HYDROXYAMIDINOPHENYLALANINE COMPOUNDS

(75) Inventor: Helmut Greiving, Hilden (DE)

(73) Assignee: Wilex AG, Munich (DE)

( * ) Notice: Subject to any disclaimer, the term of this patent is extended or adjusted under 35 U.S.C. 154(b) by 789 days.

(21) Appl. No.: 11/576,978

(22) PCT Filed: Oct. 14, 2005

(86) PCT No.: PCT/EP2005/010970
§ 371 (c)(1),
(2), (4) Date: Apr. 10, 2007

(87) PCT Pub. No.: WO2006/042678
PCT Pub. Date: Apr. 27, 2006

(65) Prior Publication Data
US 2008/0039626 A1   Feb. 14, 2008
US 2009/0099360 A9   Apr. 16, 2009

(30) Foreign Application Priority Data

Oct. 14, 2004  (EP) .................................. 04024553

(51) Int. Cl.
*C07D 295/185*  (2006.01)
(52) U.S. Cl. ...................... 544/388; 544/386; 544/387
(58) Field of Classification Search .................. None
See application file for complete search history.

(56) References Cited

FOREIGN PATENT DOCUMENTS

| | | |
|---|---|---|
| EP | 0 074 249 A | 3/1983 |
| EP | 0 861 826 A | 9/1998 |
| WO | WO 02/074756 A | 9/2002 |
| WO | WO 2004/067522 A | 8/2004 |

*Primary Examiner* — Emily Bernhardt
(74) *Attorney, Agent, or Firm* — Saul Ewing LLP

(57) ABSTRACT

The present invention relates to the preparation of 3-hydroxyamidino-phenylalanine derivatives in highly pure form which can be used for example as urokinase inhibitors. The present invention further relates to the use of high-purity 3-hydroxyamidinophenylalanine derivatives for preparing 3-amidinophenylalanine derivatives.

24 Claims, 2 Drawing Sheets

```
Peak RetTime Type  Width     Area      Height      Area
 #   [min]         [min]   mAU   *s    [mAU   ]      %
----|-------|----|-------|-----------|-----------|--------|
  1  20.240 PB   0.1030    82.22200    12.03407   0.5680
  2  21.407 BB   0.1043   1.24607e4  1795.45142  86.0758
  3  23.894 PB   0.1004   149.91762    22.68634   1.0356
  4  24.287 BB   0.0982  1297.87170   202.10693   8.9654
  5  25.388 PB   0.1693   189.13057    16.07225   1.3065
  6  27.088 BB   0.0961   296.58707    47.52221   2.0488
```

METHOD FOR PREPARING AND PURIFYING 3-HYDROXYAMIDINOPHENYLALANINE COMPOUNDS

CROSS REFERENCE TO RELATED APPLICATION

This application is a 35 USC §371 National Phase Entry Application from PCT/EP2005/010970, filed Oct. 14, 2005, and designating the United States.

DESCRIPTION

The present invention relates to the preparation of 3-hydroxyamidino-phenylalanine derivatives in highly pure form which can be used for example as urokinase inhibitors. The present invention further relates to the use of high-purity 3-hydroxyamidinophenylalanine derivatives for preparing 3-amidinophenylalanine derivatives.

The urokinase-plasminogen activator system (UPA system) plays a central role in the metastasis and, in addition, in the growth of primary tumors, for example in breast, stomach, bowel, pancreatic, ovarian cancer and other solid tumors. A medical effect can be displayed at two levels through inhibition of the UPA system: firstly blocking of metastasis, and secondly reduction of primary tumor growth. 3-Amidinophenylalanine derivatives represent a class of highly effective urokinase inhibitors.

Preparation of 3-amidinophenylalanine derivatives, in particular of N-α-(2,4,6-triisopropylphenylsulfonyl)-3-amidino-(L)-phenylalanine 4-ethoxycar-bonylpiperazide (WX-UK1), and the use thereof as urokinase inhibitors is described for example in CH-A 689611, WO 00/04954 and WO 00/17158 and in the publication by Stürzebecher et al. (Bioorg. Med. Chem. Let 9 (1999), 3147-3152). However, the synthetic methods used therein generally afford relatively low yields of product, because hydrolyzed TIPPS-OH results as unwanted by-product. One problem is that the desired reaction product can be separated from by-products only by elaborate chromatographic methods.

PCT/EP03/08230 describes methods for preparing 3-amidinophenylalanine derivatives via a 3-hydroxyamidinophenylalanine intermediate. These oxamidine derivatives represent highly specific and selective urokinase inhibitors and additionally have the advantage of oral bioavailability. However, the problem in the preparation method disclosed in PCT/EP03/08230 is that the oxamidine intermediates are not obtained in pure form, and elaborate purification methods are necessary in order to remove for example amide by-products. However, both for the further synthesis of 3-amidinophenylalanine derivatives and for a pharmaceutical use of the oxamidine derivatives, it would be advantageous for a method to be available to allow these oxamidine derivatives to be prepared in good yield and with high purity.

It was therefore the object of the present invention to provide such a method in order to obtain oxamidine derivatives in highly pure form.

This object is achieved by a method for purifying 3-hydroxyamidinophenyl-alanine derivatives, comprising the steps:

(a) addition of an aromatic sulfonic acid to a solution of an optionally contaminated 3-hydroxyamidinophenylalanine derivative in order to form a salt, (b) separation of the precipitate formed in step (a), and (c) recovery of the 3-hydroxyamidinophenylalanine derivative from the precipitate.

The meaning of "aromatic sulfonic acid" in the sense of the present invention is an aromatic or heteroaromatic mono- or oligocyclic ring system which is substituted by at least one sulfonic acid group and/or sulfonate group. The aromatic or heteroaromatic ring system may additionally have further substituents which may be selected for example from $C_1$-$C_6$-alkyl, $C_1$-$C_3$-alkoxy, hydroxyl, carboxyl, sulfonyl, nitro, cyano, oxo or/and halogen. Suitable aromatic or heteroaromatic ring systems include for example mono- and bicycles having 6 to 20 carbon atoms and 0 to 4 heteroatoms, which may preferably be selected from N, O and S.

Examples of suitable aromatic sulfonic acids are toluene- and benzene-mono- or/and -disulfonic acids, and naphthalene-mono- or/and -disulfonic acid derivatives. Disulfonic acids with a good tendency to crystallize, for example naphthalene disulfonic acids, are preferred. Naphthalene-1,5-disulfonic acid (Armstrong's acid) is most preferred. Aromatic disulfonic acids are frequently employed in the dye industry and there represent intermediates and coupling reagents for various, especially naphthalene-based, dyes.

It has now surprisingly been found that aromatic sulfonic acids, and in particular Armstrong's acid, are particularly suitable for precipitating 3-hydroxyamidinophenylalanine derivatives (oxamidines) in the form of a corresponding salt. Salts formed in this way precipitate from a solution of optionally contaminated 3-hydroxyamidinophenylalanine derivative crude products. Suitable solvents in this connection are, for example, ketones such as acetone and pentanone, esters such as ethyl acetate, polar ethers such as tetrahydrofuran, bis(2-methoxyethyl)ether (diglyme), dioxane and methyl tert-butyl ether, halogenated solvents such as dichloromethane, but also nitrites and nonpolar alcohols. The precipitates can be separated in a simple manner from the solution in a subsequent step (b), for example by filtration.

The removed salt can then be purified further by purification methods customary in the state of the art, and be dried. It is possible in this way according to the invention to improve the purity of the 3-hydroxyamidino-phenylalanine derivative even further.

Subsequently, in step (c), the 3-hydroxyamidinophenylalanine derivative is recovered. It is possible for this purpose according to the present invention to react the corresponding sulfonic acid salt for example with bases which are more basic than the hydroxyamidinophenylalanine derivatives, e.g. with sodium bicarbonate, but also with inorganic and organic bases.

The present invention thus makes it possible in a simple and elegant manner to remove contaminated reactants, intermediates and unwanted products, especially unwanted amide contaminants, from the oxamidine.

The method of the present invention is particularly suitable for purifying oxamidine compounds of the formula (I)

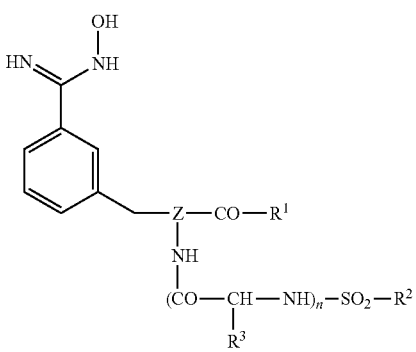

(I)

which may be in the form of racemates as well as in the form of the L or D configuration compounds, and in which
R$^1$ is a group of the formula

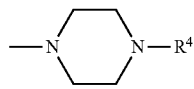

in which R$^4$ is
(i) an optionally for example C$_1$-C$_6$-alkyl-, C$_1$-C$_3$-alkoxy-, hydroxyl-, carboxyl-, sulfonyl-, nitro-, cyano-, oxo- or/and halogen-substituted C$_1$-C$_6$-alkyl residue such as, for example, ethoxycarbonyl or aryl residue such as, for example, phenyl, p-halophenyl, naphthyl,
(ii) a saturated or unsaturated branched or unbranched C$_1$-C$_6$-alkoxy residue or
(iii) an optionally for example C$_1$-C$_6$-alkyl-, C$_1$-C$_3$-alkoxy-, hydroxyl-, carboxyl-, sulfonyl-, nitro-, cyano-, oxo- or/and halogen-substituted phenoxy or benzyloxycarbonyl residue,
R$^2$ is an optionally for example C$_1$-C$_6$-alkyl-, C$_1$-C$_3$-alkoxy-, hydroxyl-, carboxyl-, sulfonyl-, nitro-, cyano-, oxo- or/and halogen-substituted phenyl residue, such as, for example, phenyl, 4-methylphenyl, 2,4,6-trimethylphenyl, 2,4,6-triisopropylphenyl, 4-methoxy-2,3,6-trimethylphenyl, R$^3$ is H or branched or unbranched C$_1$-C$_4$-alkyl, and
n is 0 or 1,
Z is N or CR$^9$ where R$^9$ is H or branched or unbranched C$_1$-C$_4$-alkyl.

According to one aspect of the invention, it can preferably be employed in order to isolate N-α-(2,4,6-triisopropylphenylsulfonyl)-3-hydroxyamidino-(L)-phenylalanine 4-ethoxycarbonylpiperazide in highly pure form.

In the synthetic methods disclosed to date for preparing oxamidine derivatives, the oxamidine compound results in a low degree of purity and comprises a large proportion of up to 30% of amide contaminant and further contaminations by reactants and unknown compounds. It is possible with the method of the present invention to obtain pure oxamidine. The oxamidine preferably results in a purity of more than 90%, more preferably more than 95% and most preferably more than 99%.

According to a further aspect of the present invention, no racemization takes place in the purification method of the invention, so that enantiopure oxamidine products are obtained.

In one embodiment of the invention, the purification according to the invention can be part of a method for preparing 3-hydroxyamidinophenyl-alanine derivatives. A preferred preparation method includes the steps:
(i) reaction of an N-protected 3-cyanophenylalanine with a piperazine derivative to form an N-protected 3-cyanophenylalanine piperazide,
(ii) reaction with an optionally substituted phenylsulfonyl halide, in particular a TIPPS halide;
(iii) conversion of the cyano group into a hydroxyamidino group
(iv) purification with an aromatic sulfonic acid as described above.

In step (i) of the method of the invention, an N-protected 3-cyanophenyl-alanine is reacted with a piperazine derivative. The term "piperazine derivative" includes in the sense of the present invention piperazine and its derivatives, wherein optionally up to four carbon positions in the ring and/or not more than one nitrogen atom in the ring may be substituted. Piperazine derivatives preferably employed have a substituent on one of the two nitrogen atoms in the ring.

Examples of suitable substituents include C$_1$-C$_6$-alkyl residues, saturated or unsaturated branched or unbranched C$_1$-C$_6$-alkoxy residues, phenoxy and phenyloxycarbonyl residues, and aryl residues such as, for example, phenyl, p-halophenyl and naphthyl. These may in turn be optionally substituted in each case independently, for example by C$_1$-C$_6$-alkyl, C$_1$-C$_3$-alkoxy, hydroxyl, carboxyl, sulfonyl, nitro, cyano, oxo or/and halogen.

It is possible according to the present invention to employ any protective group for protecting the amino nitrogen atom of the 3-cyanophenylalanine employed in step (i). Examples of suitable protective groups for amino functions are known in the prior art and include for example Cbz (benzyloxycarbonyl), Boc (T-butyloxycarbonyl), DIMOZ (dimetoxybenzyl-oxycarbonyl), Tfac (trifluoroacetyl), CyOC (cyano-t-butyloxycarbonyl), Phth (phthaloyl), Bpoc (2-biphenyl-4-isopropoxycarbonyl), Ddz (3,5-dimethoxyphenylisopropoxycarbonyl), Fmoc (fluorenyl-9-methyloxycarbonyl), PALOC (3-(3-pyridyl) allyloxycarbonyl), Tos (p-toluenesulfonyl), NPS (2-nitrophenyl-sulfenyl), DNPS (2,4-dinitrophenylsulfenyl). Boc is particularly preferably employed as protective group according to the present invention.

The reaction in step (i) of the method according to the invention forms an N-protected 3-cyanophenylalanine piperazide.

It is subsequently possible in one embodiment of the invention to remove the N-protective group again. The conditions necessary for eliminating the respective protective group are known to a skilled worker. The Boc protective group which is particularly preferably used according to the invention can be eliminated for example in acidic medium, e.g. in an organic solvent such as dioxane or methanol which is saturated with HCl gas or trifluoroacetate, particularly preferably with 4M HCl (g) in dioxane. An alternative possibility is to choose the conditions in the subsequent reaction step (ii) so that elimination of the protective group takes place in situ.

In step (ii), the 3-cyanophenylalanine piperazide formed in step (i) is reacted with a phenylsulfonyl halide, which may optionally be substituted.

Preferred halides in this connection are fluoride, chloride, bromide and iodide. Examples of substituents on the phenylsulfonyl halide include $C_1$-$C_6$-alkyl, $C_1$-$C_3$-alkoxy, hydroxyl, carboxyl, sulfonyl, nitro, cyano, oxo and halogen. Phenylsulfonyl halides which are preferably employed are phenyl-, 4-methylphenyl-, 2,4,6-trimethylphenyl-, 4-methoxy-2,3,6-trimethylphenyl- and especially 2,4,6-triisopropylphenylsulfonyl (TIPPS) halides.

In step (iii), the cyano group is converted into the hydroxyamidino function. This conversion can be carried out for example by means of hydroxylamine hydrochloride in the presence of sodium carbonate or triethylamine. Suitable methods for such reactions are known in the prior art and are described for example in WO 03/072559.

The 3-hydroxyamidinophenylalanine derivative formed in step (iii) is subsequently obtained in highly pure form in accordance with the purification method described above using an organic sulfonic acid. It is unnecessary in this connection first to isolate the 3-hydroxyamidinophenyl-alanine derivative from step (iii).

3-Hydroxyamidinophenylalanine derivatives are obtained in this way with little expenditure on apparatus and in high chemical yield and purity.

The oxamidine compounds obtained in highly pure form with the method of the invention can be employed for example as orally available urokinase inhibitors.

According to a further aspect of the present invention, the oxamidine compounds can be reacted further to give 3-amidinophenylalanine derivatives. Since oxamidine is in highly pure form according to the present invention, the yield of amidino final product in the further course of the synthesis is also distinctly increased.

The present invention thus provides a method for preparing 3-amidino-phenylalanine derivatives including the steps:

(i) preparation of a 3-hydroxyamidinophenylalanine derivative by a method described above, and (ii) conversion of the hydroxyamidino group into an amidino group.

The hydroxyamidino group can be converted into the amidino derivative by reduction. This normally takes place by catalytic hydrogenation in reactions familiar to the skilled worker, for example as indicated in WO 03/076391, WO 03/072559, EP 1 294 742, and in Steinmetzer et al., J. Enzyme Inhibition, 16, 2001, 241-249, Kent et al., J. Peptide Res., 52, 1998, 201-207 and Stüber et al., peptide Res. 8, 1995, 78-85.

It is thus possible by the method of the invention to isolate the corresponding 3-amidinophenylalanine derivative with a yield which is distinctly improved by comparison with methods known in the prior art, and in highly pure form.

FIGURES

EXAMPLE

Step 1: Alkylation and Decarboxylation

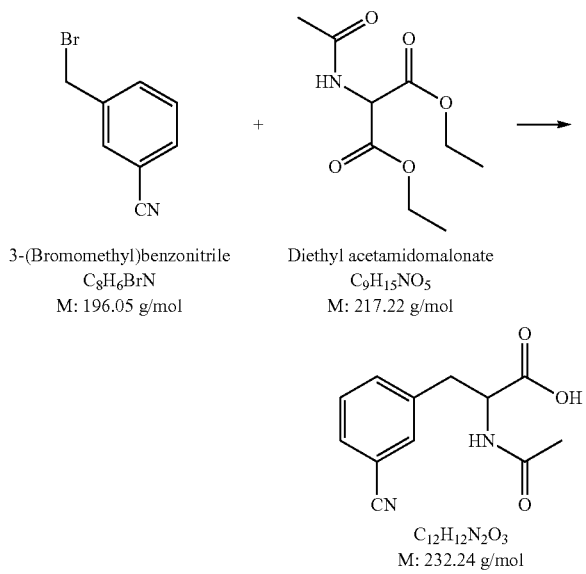

Figure 1:
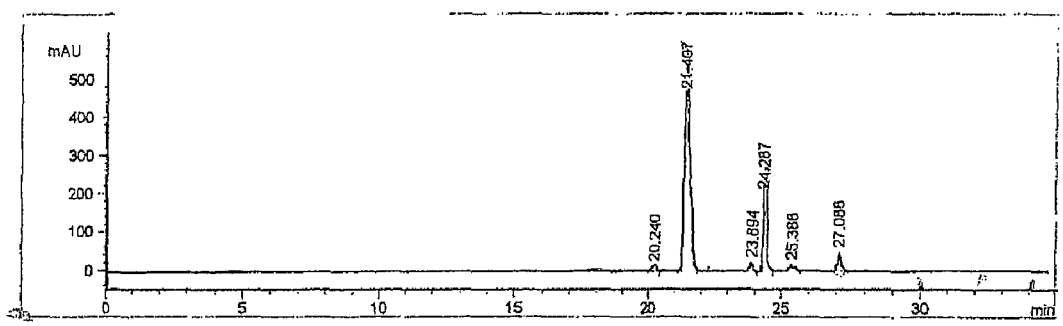
FIG. 1 shows an HPLC profile of the product mixture obtained in a conventional synthesis of N-alpha-(2,4,6-triisopropylphenylsulfonyl)-3-hydroxyamidino-(L)-phenylalanine 4-ethoxycarbonylpiperazide. The oxamidine is detected at a retention time of about 21.4 minutes, followed by the amide contaminant at 24.3 minutes.
Figure 2:
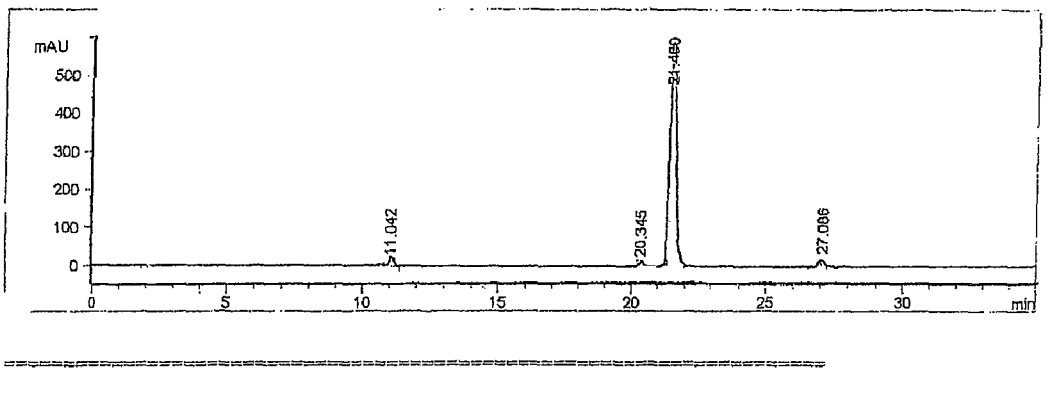
FIG. 2 shows an HPLC profile of the oxamidine N-alpha-(2,4,6-triiso-propylphenylsulfonyl)-3-hydroxyamidino-(L)-phenylalanine 4-ethoxy-carbonylpiperazide prepared by the method of the invention.

3-(Bromomethyl)benzonitrile
$C_8H_6BrN$
M: 196.05 g/mol

Diethyl acetamidomalonate
$C_9H_{15}NO_5$
M: 217.22 g/mol $C_{12}H_{12}N_2O_3$
M: 232.24 g/mol Diethyl acetamidomalonate (407 g) is added to ethanol (1 l) at room temperature in a nitrogen atmosphere. The suspension is heated to about 70° C., and a solution of sodium ethoxide (130 g) in ethanol (900 ml) is added. The reaction mixture is stirred at this temperature for a further 30 minutes. A suspension of 3-bromomethylbenzonitrile (300 g) in ethanol (1.4 l) is then added to the reaction vessel. The temperature in the reaction vessel is kept at about 70° C. for a further 2.5 hours. Then, over the course of 1.5 hours, dilute sodium hydroxide solution (2N, 2.2 l) is added dropwise. The suspension is stirred at about 70° C. for a further 30 minutes and then cooled to room temperature. The pH of the reaction mixture is slowly reduced at room temperature to about 7 by adding concentrated hydrochloric acid (over the course of about 1 hour). The organic solvent is removed by distillation under reduced pressure (<100 mbar; $T_{max}$=60° C.). The remaining residue is dissolved in 1N NaOH (1 l). The aqueous solution is extracted 3 times with ethyl acetate (350 ml each time). This is followed by cooling to 10° C. The aqueous solution is acidified with conc. HCl (pH=1). The desired product is extracted with ethyl acetate (3 extractions with 1.2 l of ethyl acetate each time). The combined organic phases are concentrated under reduced pressure. The desired product precipitates as a white solid. The crystals are collected in a suction funnel at 5° C., washed with small amounts of ethyl acetate and dried at 45° C. in a nitrogen atmosphere.

Yield: 243 g (68%).

Step 2: Enzymatic Racemate Resolution

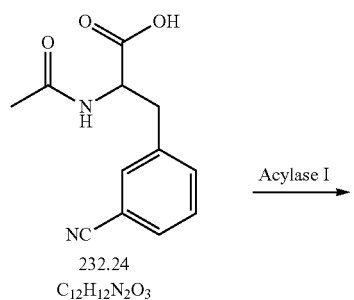

232.24
C₁₂H₁₂N₂O₃

Acylase I →

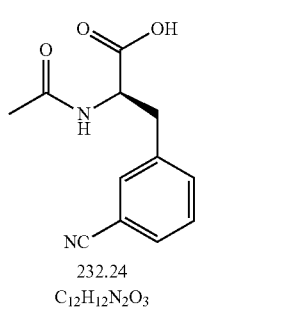 + 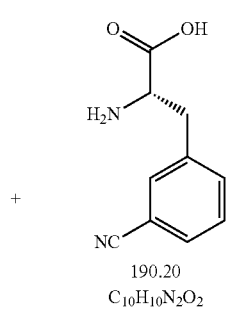

232.24
C₁₂H₁₂N₂O₃

190.20
C₁₀H₁₀N₂O₂

Acetylcyanophenylalanine (940 g) is dissolved in 1N NaOH (4 l) at 37° C. The initial pH of 12.8 is reduced to 7.2 by adding 4N HCl (approximately 120 ml). Acylase I (37.8 g) is added. In order to keep the pH of the reaction mixture constant at about 7.2, NaOH (1N) is continuously added to the reaction mixture. After 72 hours at 37° C., the precipitated product is isolated by filtration at 20° C. The crystals are washed with water and dried under reduced pressure at about 40° C. Concentration of the filtrate under reduced pressure to one third of the original volume leads to precipitation of further product.

Overall yield: 261 g (34%).

Step 3: Protection of the NH₂ Functionality with Boc

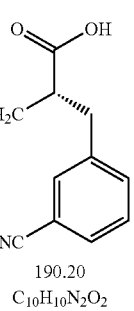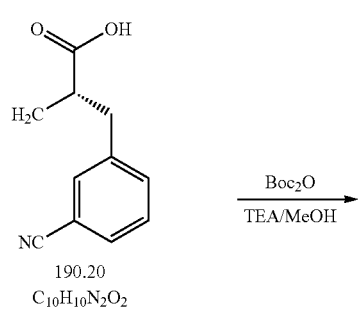

190.20
C₁₀H₁₀N₂O₂

Boc₂O / TEA/MeOH →

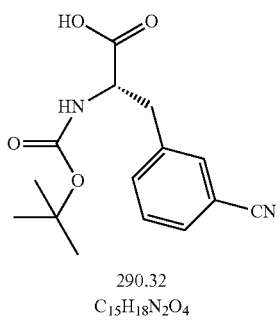

290.32
C₁₅H₁₈N₂O₄

Triethylamine (310 ml) is added to a suspension of cyanophenyl-L-alanine (425 g) in methanol (4.5 l). At 25° C., di-tert-butyl dicarbonate (488 g) is added. The reaction mixture is stirred overnight. The organic solvent is removed under reduced pressure at 40° C. The remaining orange-colored oil is diluted with ethyl acetate (3 l). 1N HCl (2.3 l) is added, and the heterogeneous solution is stirred vigorously for 30 minutes. A phase separation is carried out. The organic phase is isolated, extracted with water and dried with MgSO₄. After filtration, the organic phase is evaporated to dryness under reduced pressure at 40° C. Crystals are obtained on addition of dichloromethane to the residue. The crystals are collected by filtration and dried under nitrogen at 45° C.

Yield: 554 g (85%)

Step 4: Coupling Reaction

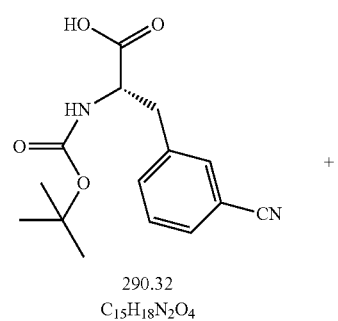

290.32
C₁₅H₁₈N₂O₄

+

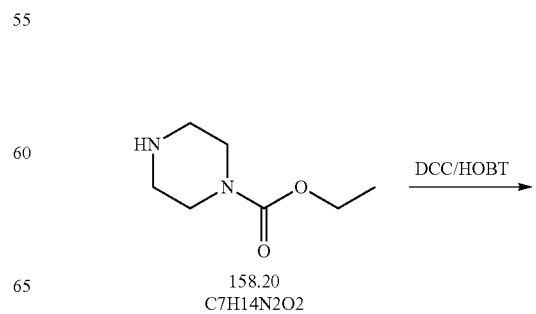

158.20
C7H14N2O2

DCC/HOBT →

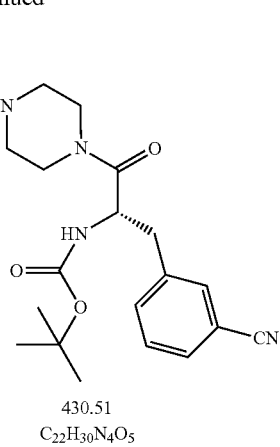

430.51
$C_{22}H_{30}N_4O_5$

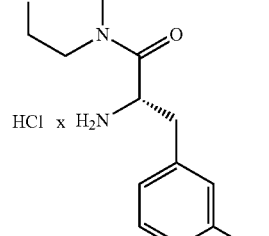

330.39 + 36.5 = 366.9
$C_{17}H_{22}N_4O_3$

Boc-Cyanophenylalanine (554 g) and HOBT (52 g) are suspended in dichloromethane (2.7 l). A solution of DCC (453 g) in dichloromethane (1 l) is added. The suspension is then cooled to 10-15° C., and ethoxycarbonyl-piperazine (347 g) is added dropwise over the course of 30 minutes while maintaining the above temperature range. The reaction mixture is stirred overnight. The urea is filtered off and discarded. Saturated NaHCO$_3$ solution (1.8 l) is added to the filtrate. The heterogeneous mixture is stirred for 30 minutes and then the phases are separated. The organic phase is extracted with water (2 l) and then dried with MgSO$_4$. The MgSO$_4$ is filtered off and the solution is concentrated under reduced pressure at 30° C. The remaining oil is dissolved in ethyl acetate (300 ml). The solution is heated to the boiling point. Diisopropyl ether (750 ml) is slowly added until the solution becomes cloudy. The temperature is reduced to 50° C., and the mixture is left to settle. The temperature is then reduced over the course of 5 hours to 25° C. The product is filtered off and washed with diisopropyl ether and then dried under nitrogen at 40° C.

Yield: 660 g (80%)

Boc-L-Cyanophenylalanine pipamide (442 g) is dissolved in a solution of HCl in dioxane (4N, 1.2 l). The temperature rises during the addition from 25° C. to 32° C. The reaction is complete after 3 hours, and dichloromethane (1 l) is added to the solution. The desired product starts to precipitate. The suspension is stirred overnight. An excess of HCl is removed by evacuating the mixture. The product is isolated by filtration, washed with diisopropyl ether (0.7 l) and dried under high vacuum at 45° C.

Yield: 552 g (98%)

Step 6: Sulfonamide Formation

Step 5: Deprotection

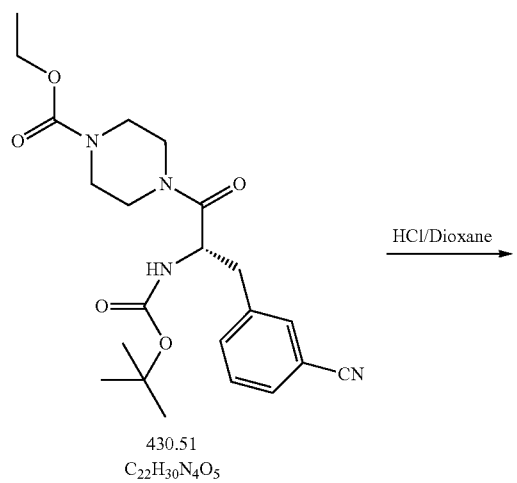

430.51
$C_{22}H_{30}N_4O_5$

HCl/Dioxane →

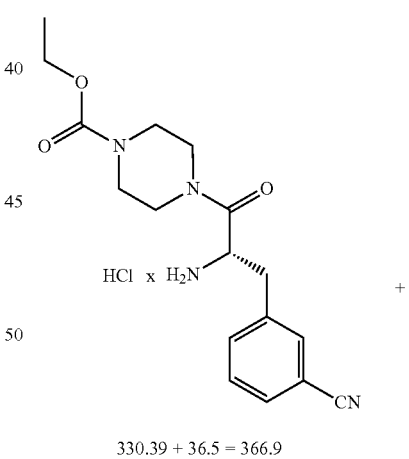

330.39 + 36.5 = 366.9
$C_{17}H_{22}N_4O_3 \times HCL$

+

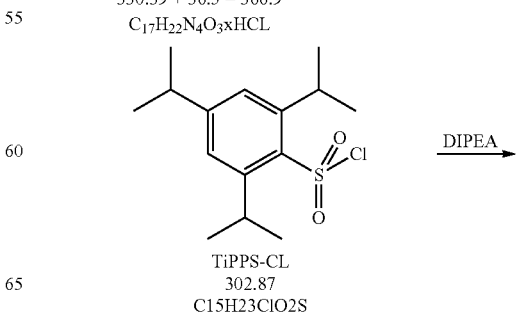

TiPPS-CL
302.87
C15H23ClO2S

DIPEA →

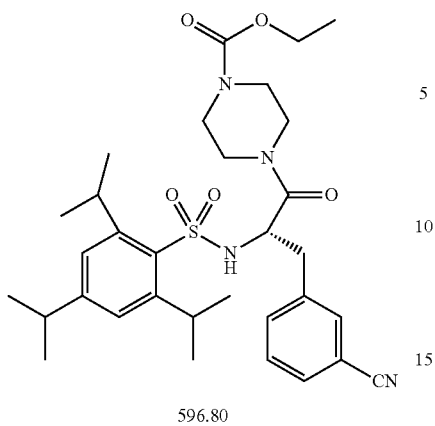

596.80
C32H44N4O5S 2,4,6-Triisopropylphenylsulfonyl chloride (212 g) is added to a suspension of cyanophenyl-L-alanine pipamide HCl (257 g) in dichloromethane (1.6 l) at 25° C. Addition of N-ethyldiisopropylamine (238 ml) results in a clear solution. The addition proceeds exothermically (temperature increase from 25° C. to 35° C.). Water (1.1 l) is added to the reaction mixture after it has been stirred at room temperature for 2 hours. The phases are separated, and the organic phase is extracted once with saturated NaHCO$_3$ solution (1.6 l) and once with water (0.5 l). The organic phase is dried with MgSO$_4$, filtered and concentrated under reduced pressure. A colorless oil is obtained and slowly crystallizes on standing at room temperature.

Yield: 423 g (~100%)

Step 7: Amide Oxime Formation; N-alpha-(2,4,6-triisopropylphenylsulfonyl)-3-hydroxyamidino-(L)-phenylalanine-4 Ethoxycarbonylpiperazide

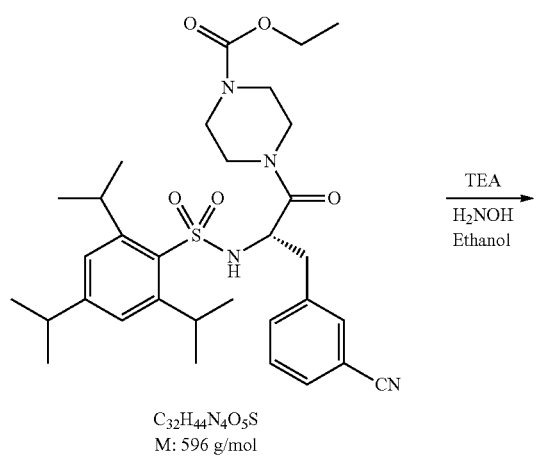

C32H44N4O5S
M: 596 g/mol

TEA
H$_2$NOH
Ethanol

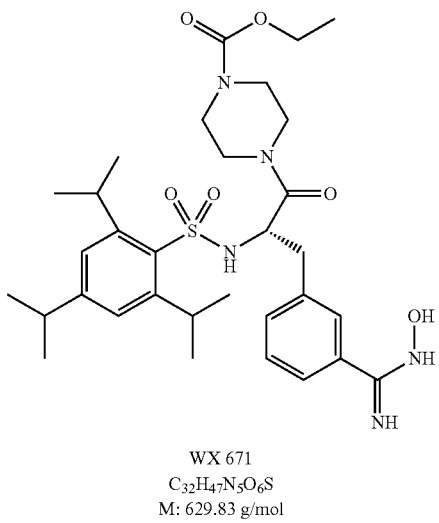

WX 671
C32H47N5O6S
M: 629.83 g/mol

TIPPS-L-Cyanophenylalanine pipamide (50 g) is dissolved in ethanol (350 ml). Hydroxylamine HCl (7.3 g) and triethylamine (14.5 ml) are successively added. The reaction mixture is heated to the boiling point (~75° C.) and heated under reflux for 6 hours. It is then cooled to 40° C., and the solvent is replaced. Ethanol is removed under reduced pressure and dichloromethane (300 ml) and water (100 ml) are added to the residue. A phase separation is carried out. The organic phase is dried with MgSO$_4$. Filtration is followed by removal of the solvent under reduced pressure.

A white solid (57 g) is obtained and is dissolved in acetone (200 ml). A solution of Armstrong's acid (15 g) in acetone (150 ml) is added. The mixture is heated at the boiling point of acetone for 30 minutes. The Armstrong salt of the desired product crystallizes as white solid. The suspension is cooled to room temperature and stirred for 1 hour before subsequently carrying out a filtration. The crystals are washed with acetone (75 ml), dried and then dissolved in dichloromethane (600 ml). Saturated NaHCO$_3$ solution (400 ml) is added. The heterogeneous mixture is stirred vigorously for 20 minutes and then the phases are separated. The organic phase is extracted with water (400 ml), and then the dichloromethane is removed by distillation. A white solid (45 g) is obtained. The product is recrystallized from ethyl acetate/diisopropyl ether, dissolving 45 g in ethyl acetate (60 ml). Diisopropyl ether (250 ml) is added. The suspension formed in this way is heated at the boiling point for 30 minutes and then slowly cooled to room temperature. The amorphous white solid is filtered off, washed with diisopropyl ether and dried in vacuo at 45° C.

Yield: 34 g (65%)

The invention claimed is:

1. A method for purifying a 3-hydroxyamidinophenylalanine compound having the formula (I):

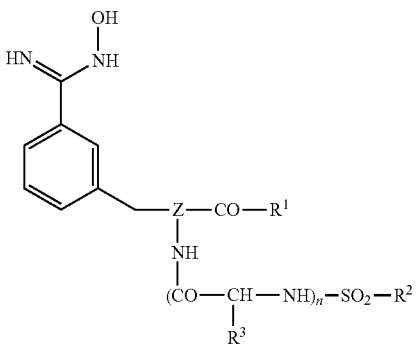

in which $R^1$ is a group of the formula

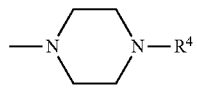

in which $R^4$ is
(i) an unsubstituted $C_1$-$C_6$-alkyl residue, or a $C_1$-$C_6$-alkyl-, $C_1$-$C_3$-alkoxy-, hydroxyl-, carboxyl-, nitro-, cyano-, or/and halogen-substituted $C_1$-$C_6$-alkyl residue;
(ii) a saturated or unsaturated branched or unbranched $C_1$-$C_6$-alkoxy residue;
(iii) an unsubstituted phenoxy or benzyloxycarbonyl residue, a $C_1$-$C_6$-alkyl-, $C_1$-$C_3$-alkoxy-, hydroxyl-, carboxyl-, nitro-, cyano-, or/and halogen-substituted phenoxy or benzyloxycarbonyl residue;
(iv) phenyl, p-halophenyl, or naphthyl, or
(v) ethoxycarbonyl, $R^2$ is an unsubstituted phenyl residue, or a $C_1$-$C_6$-alkyl-, $C_1$-$C_3$-alkoxy-, hydroxyl-, carboxyl-, nitro-, cyano-, or/and halogen-substituted phenyl residue, $R^3$ is H or branched or unbranched $C_1$-$C_4$-alkyl, n is 0 or 1, and Z is $CR^9$ where $R^9$ is H, comprising the steps of:
(a) forming a salt precipitate by adding an aromatic sulfonic acid to a solution of a contaminated 3-hydroxyamidinophenylalanine compound,
(b) separating said precipitate formed in step (a), and
(c) recovering a purified 3-hydroxyamidinophenylalanine compound from the precipitate.

2. The method as claimed in claim 1, wherein the 3-hydroxyamidinophenylalanine compound is an N-α-(2,4,6-triisopropylphenylsulfonyl-3-hydroxyamidino-(D,L)-phenylalanine compound or a L enantiomer thereof.

3. The method of claim 1, wherein $R^4$ is ethoxycarbonyl, phenyl, p-halophenyl, or naphthyl.

4. The method as claimed in claim 3, in which the aromatic sulfonic acid in step (a) is Armstrong's acid.

5. The method as claimed in claim 3, wherein a solution of the 3-hydroxyamidinophenylalanine compound in acetone is employed in step (a).

6. The method as claimed in claim 3, wherein said separation of the precipitate in step (b) takes place by filtration.

7. The method as claimed in claim 3, wherein the recovery in step (c) takes place by reaction with $NaHCO_3$.

8. The method as claimed in claim 3, wherein the 3-hydroxyamidinophenylalanine compound is obtained in a purity of more than 90%.

9. The method as claimed in claim 3, wherein the 3-hydroxyamidinophenylalanine compound is obtained in a purity of more than 95%.

10. The method as claimed in claim 3, wherein the hydroxyamidinophenylalanine compound is obtained in a purity of more than 99%.

11. The method of claim 3, wherein $R^2$ is phenyl, 4-methylphenyl, 2,4,6-trimethylphenyl, 2,4,6-triisopropylphenyl, or 4-methoxy-2,3,6-trimethylphenyl.

12. A method for preparing a 3-hydroxyamidinophenylalanine compound having the formula (I):

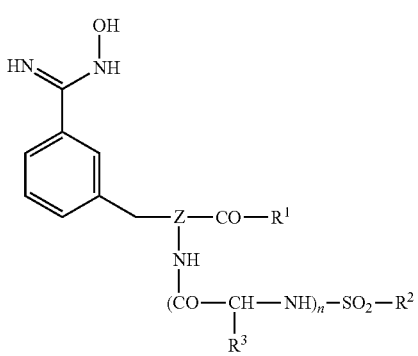

in which $R^1$ is a group of the formula

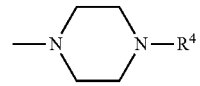

in which $R^4$ is
(i) an unsubstituted $C_1$-$C_6$-alkyl residue, or a $C_1$-$C_6$-alkyl-, $C_1$-$C_3$-alkoxy-, hydroxyl-, carboxyl-, nitro-, cyano-, or/and halogen-substituted $C_1$-$C_6$-alkyl residue;
(ii) a saturated or unsaturated branched or unbranched $C_1$-$C_6$-alkoxy residue;
(iii) an unsubstituted phenoxy or benzyloxycarbonyl residue, a $C_1$-$C_6$-alkyl-, $C_1$-$C_3$-alkoxy-, hydroxyl-, carboxyl-, nitro-, cyano-, or/and halogen-substituted phenoxy or benzyloxycarbonyl residue,
(iv) phenyl, p-halophenyl, or naphthyl, or
(v) ethoxycarbonyl;

$R^2$ is an unsubstituted phenyl residue, or a $C_1$-$C_6$-alkyl-, $C_1$-$C_3$-alkoxy-, hydroxyl-, carboxyl-, nitro-, cyano-, or/and halogen-substituted phenyl residue, $R^3$ is H or branched or unbranched n is 0, and Z is $CR^9$ where $R^9$ is H, comprising the steps of:
(i) reacting an N-protected 3-cyanophenylalanine with a piperazine derivative to form an N-protected 3-cyanophenylalanine piperazide, wherein said piperazine derivative is of the formula:

(ii) deprotecting said N-protected 3-cyanophenylalanine piperazide to form an N-deprotected 3-cyanophenylalanine piperazide and reacting said N-deprotected 3-cyanophenylalanine piperazide with a phenylsulfonyl halide to form a compound, said phenylsulfonyl halide being optionally substituted with a substituent, wherein said substituent is C1-C6-alkyl, C1-C3-alkoxy, hydroxyl, carboxyl, nitro, cyano and/or halogen;

(iii) converting a cyano group of the compound formed in step (ii) into a hydroxyamidino group to form a 3-hydroxyamidinophenylalanine compound (iv) purifying the 3-hydroxyamidinophenylalanine compound formed in step (iii) by:

(A) forming a salt precipitate by adding an aromatic sulfonic acid to a solution of said 3-hydroxyamidinophenylalanine compound;

(B) separating said precipitate formed in step (A); and (C) recovering a purified 3-hydroxyamidinophenylalanine compound from the precipitate.

13. The method of claim 12, wherein the piperazine derivative in step (i) is ethoxycarbonylpiperazine.

14. The method of claim 12, wherein $R^4$ is ethoxycarbonyl, phenyl, p-halophenyl, or naphthyl.

15. The method of claim 14 wherein a Boc N-protected 3-cyanophenylalanine derivative is employed in step (i).

16. The method of claim 14, wherein $R^2$ is phenyl, 4-methylphenyl, 2,4,6-trimethylphenyl, 2,4,6-triisopropylphenyl, or 4-methoxy-2,3,6-trimethylphenyl.

17. The method of claim 14, wherein said phenylsulfonyl halide is 2,4,6-triisopropylbenzenesulfonyl chloride.

18. The method of claim 14, wherein the cyano group in step (iii) is converted into a hydroxyamidino group by reaction with hydroxylamine hydrochloride in the presence of sodium carbonate or triethylamine.

19. The method of claim 14, wherein the 3-hydroxyamidinophenylalanine compound is produced in a purity of more than 90%.

20. The method of claim 14, wherein the 3-hydroxyamidinophenylalanine compound is produced in a purity of more than 95%.

21. The method of claim 14, wherein the 3-hydroxyamidinophenylalanine compound is produced in a purity of more than 99%.

22. A process for preparing a 3-amidinophenylalanine compound comprising the steps of:

I) preparing a hydroxyamidinophenylalanine compound having the formula (I):

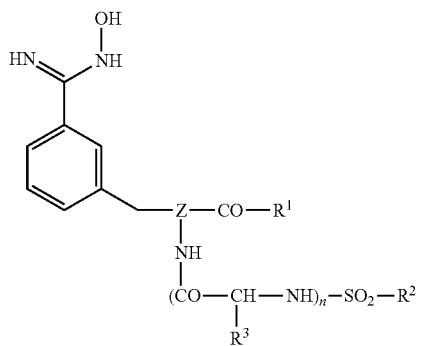

in which $R^1$ is a group of the formula

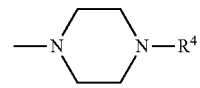

in which $R^4$ is
(i) an unsubstituted $C_1$-$C_6$-alkyl residue, or a $C_1$-$C_6$-alkyl-, $C_1$-$C_3$-alkoxy-, hydroxyl-, carboxyl-, nitro-, cyano-, or/and halogen-substituted $C_1$-$C_o$-alkyl residue;
(ii) a saturated or unsaturated branched or unbranched $C_1$-$C_6$-alkoxy residue;
(iii) an unsubstituted phenoxy or benzyloxycarbonyl residue, a $C_1$-$C_6$-alkyl-, $C_1$-$C_3$-alkoxy-, hydroxyl-, carboxyl-, nitro-, cyano-, or/and halogen-substituted phenoxy or benzyloxycarbonyl residue; or
(iv) an aryl residue,
$R^2$ is an unsubstituted phenyl residue, or a $C_1$-$C_6$-alkyl-, $C_1$-$C_3$-alkoxy-, hydroxyl-, carboxyl-, nitro-, cyano-, or/and halogen-substituted phenyl residue,
$R^3$ is H or branched or unbranched $C_1$-$C_4$-alkyl,
n is 0, and
Z is $CR^9$ where $R^9$ is H,
comprising the steps of:
(i) reacting an N-protected 3-cyanophenylalanine with a piperazine derivative to form an N-protected 3-cyanophenylalanine piperazide, wherein said piperazine derivative is of the formula:

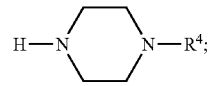

(ii) deprotecting said N-protected 3-cyanophenylalanine piperazide to form an N-deprotected 3-cyanophenylalanine piperazide and reacting said N-deprotected 3-cyanophenylalanine piperazide with a phenylsulfonyl halide to form a compound, said phenylsulfonyl halide being optionally substituted with a substituent, wherein said substituent is C1-C6-alkyl, C1-C3-alkoxy, hydroxyl, carboxyl, nitro, cyano and/or halogen;

(iii) converting a cyano group of the compound formed in step (ii) into a hydroxyamidino group to form a 3-hydroxyamidinophenylalanine compound (iv) purifying the 3-hydroxyamidinophenylalanine compound formed in step (iii) by:

(A) forming a salt precipitate by adding an aromatic sulfonic acid to a solution of said 3-hydroxyamidinophenylalanine compound;
(B) separating said precipitate formed in step (A); and
(C) recovering a purified 3-hydroxyamidinophenylalanine compound from the precipitate; and II) converting a hydroxyamidino group of said 3-hydroxyamidinophenylalanine compound into an amidino group to form a 3-amidinophenylalanine compound.

23. The method as claimed in claim 22, in which the hydroxyamidino group is converted into an amidino group in step (ii) by reaction with acetic anhydride and subsequent catalytic hydrogenation.

24. A method for purifying a 3-hydroxyamidinophenylalanine compound wherein the 3-hydroxyamidinophenylalanine compound is N-α-2,4,6-triisopropylphenylsulfonyl-3-hydroxyamidino-(D,L)-phenylalanine, 4-ethoxycarbonylpiperazine or a L enantiomer thereof, comprising the steps of:
(a) forming a salt precipitate by adding an aromatic sulfonic acid to a solution of a contaminated 3-hydroxyamidinophenylalanine compound,
(b) separating said precipitate formed in step (a), and
(c) recovering a purified 3-hydroxyamidinophenylalanine compound from the precipitate.

* * * * *